United States Patent
Gillespie (12)

(10) Patent No.: US 6,207,617 B1
(45) Date of Patent: Mar. 27, 2001

(54) CONCENTRATE COMPOSITION OF PLANT TREATMENT COMPOUND IN ACID FORM

(75) Inventor: Jane L. Gillespie, St. Louis, MO (US)

(73) Assignee: Monsanto Compant, St. Louis, MO (US)

( * ) Notice: Subject to any disclaimer, the term of this patent is extended or adjusted under 35 U.S.C. 154(b) by 0 days.

(21) Appl. No.: 09/298,766

(22) Filed: Apr. 23, 1999

Related U.S. Application Data

(60) Provisional application No. 60/082,957, filed on Apr. 24, 1998.

(51) Int. Cl.$^7$ .............................. A01N 25/32; A01N 57/02
(52) U.S. Cl. ............................................. 504/206; 504/362
(58) Field of Search ...................................... 504/206, 362

(56) References Cited

U.S. PATENT DOCUMENTS

| | | | |
|---|---|---|---|
| 3,799,758 | 3/1974 | Franz | 71/86 |
| 4,931,080 | 6/1990 | Chan et al. | 71/87 |
| 5,075,058 | 12/1991 | Chan et al. | 264/118 |
| 5,100,667 | 3/1992 | Chan et al. | 424/405 |
| 5,389,680 | 2/1995 | Ruminski | 514/563 |
| 5,464,806 | 11/1995 | Kassebaum et al. | 504/206 |
| 5,663,117 | * 9/1997 | Warner et al. | 504/206 |
| 5,888,934 | * 3/1999 | Townson et al. | 504/206 |

FOREIGN PATENT DOCUMENTS

| | | | |
|---|---|---|---|
| 91/08666 | 6/1991 | (WO) | A01N/25/12 |
| 94/19941 | 9/1994 | (WO) | A01N/25/04 |
| 95/16351 | 6/1995 | (WO) | A01N/25/30 |
| 97/00010 | 1/1997 | (WO) | A01N/25/30 |

* cited by examiner

*Primary Examiner*—S. Mark Clardy
(74) *Attorney, Agent, or Firm*—James C. Forbes; Ira D. Finkelstein; Howrey Simon Arnold & White, LLP

(57) ABSTRACT

There is provided a concentrate composition, suitable for foliar application to a plant to elicit a biological activity therein, comprising (a) about 20% to about 90% by weight of a plant treatment compound that is an acid having a solubility in deionized water at 25° C. of less than about 50 g/l and is present predominantly in the acid form, and (b) a surfactant of formula $$R-O-(CH_2CH_2O)_n-H$$

wherein R is a straight or branched chain aliphatic hydrocarbyl group having about 24 to about 60 carbon atoms and n is an integer having an average value of about 5 to about 100. The weight ratio of the surfactant to the plant treatment compound is about 1:2 to about 1:30. In a particular embodiment, the composition is a liquid suspension concentrate having a continuous aqueous phase and a discontinuous particulate phase comprised predominantly of the plant treatment compound. The plant treatment compound can be a herbicide, for example glyphosate.

13 Claims, No Drawings

CONCENTRATE COMPOSITION OF PLANT TREATMENT COMPOUND IN ACID FORM

This application claims the benefit of provisional application Serial No. 60/082,957 filed Apr. 24, 1998.

FIELD OF THE INVENTION

This invention relates to formulations of plant treatment compounds. In particular, this invention relates to concentrate formulations which, following dilution, dissolution or dispersion in water, are applied to foliage of a plant.

A plant treatment compound, as defined herein, is a chemical substance, whether naturally or synthetically derived, which is applied to a plant to result in expressing a desired biological activity. By "biological activity" is meant the elicitation of a stimulatory, inhibitory, regulatory, therapeutic, toxic or lethal response in the plant or in a pathogen, parasite or feeding organism present in or on the plant.

A concentrate composition, as defined herein, contains at least about 20% by weight, and up to about 90% by weight, in total of one or more plant treatment compounds.

The present invention applies particularly to a class of foliar-applied plant treatment compounds that are acidic. As conventionally defined, an acid is a proton donor. A compound described herein as an "acid" or in an "acid form" is to be understood as having a molecular structure with one or more proton-donating groups, in none of which is the proton substituted by a salt-forming cation. A salt-forming cation herein means any cationic entity other than a proton. It will be recognized, however, that a formulation containing a plant treatment compound in acid form can also contain a salt of the plant treatment compound.

Plant treatment compounds to which the invention can usefully be applied include, but are not limited to, chemical pesticides (such as herbicides, algicides, fungicides, bactericides, viricides, insecticides, aphicides, miticides, nematicides and molluscicides), plant growth regulators, fertilizers and nutrients, gametocides, defoliants, desiccants, mixtures thereof, and the like. The invention has particular application for such compounds if they are capable of existing in an acid form and eliciting a biological response as described above in such acid form.

BACKGROUND OF THE INVENTION

Plant treatment compounds, including foliar-applied herbicides, have often been formulated as concentrates with a surfactant. When water is added to such a concentrate, the resulting sprayable composition is, by virtue of the surfactant provided therein, more easily and effectively retained on foliage (ie., leaves and other photosynthesizing organs) of plants. Surfactants can also provide other benefits, including improved contact of spray droplets with a waxy leaf surface and, in some cases, improved penetration of the accompanying plant treatment compound into the interior of leaves. Through these and perhaps other effects, particular surfactants have long been known to increase the biological effectiveness of herbicide compositions, or other compositions of plant treatment compounds, when present in such compositions.

Thus, for example, the herbicide glyphosate (N-phosphonomethylglycine), usually in the form of a water-soluble salt thereof, has been formulated with surfactants such as those having polyoxyalkylene (polyoxyethylene and/or polyoxypropylene) moieties, including, among other surfactants, polyoxyalkylene alkylamines.

The term "alkyl" as an element in the description of a surfactant herein is used in the sense in which it is conventionally used in surfactant-related art to embrace unsaturated as well as saturated hydrocarbyl chains, and includes linear and branched chains. In general, alkyl groups useful as hydrophobic moieties in surfactants contain about 8 to about 22, most commonly about 12 to about 18, carbon atoms.

Surfactants have been combined with glyphosate or other plant treatment compounds in (a) liquid or solid concentrate compositions provided by the supplier and diluted, dissolved or dispersed in water by the user before application, (b) ready-to-use dilute aqueous compositions provided by the supplier and applied without further dilution by the user, and (c) user-prepared dilute aqueous compositions made by adding separate compositions of plant treatment compound (e.g., glyphosate) and surfactant to water prior to application. Such user-prepared dilute aqueous compositions are known as "tank-mix" compositions.

Some surfactants, although chemically stable, are physically incompatible with certain plant treatment compounds, particularly in aqueous liquid concentrate compositions. For example, an aqueous micellar solution of most classes of nonionic surfactant, including polyoxyethylene alkylether surfactants, does not tolerate the presence of high concentrations of salts imparting high ionic strength to the solution. This is true, for example, of a polyoxyethylene alkylether surfactant in a concentrated aqueous solution of a salt of glyphosate. Such physical incompatibility can be manifested immediately on preparation of the composition, or over time or when exposed to certain temperature conditions or regimes, leading to inadequate shelf-life of the composition. A common effect of physical incompatibility is separation of the composition into distinct phases. Other problems that can arise from such incompatibility include formation of aggregates large enough to interfere with commercial handling and application, for example by blocking spray nozzles.

Many plant treatment compounds are commercially packaged as a liquid concentrate formulation that, while being a concentrate, nevertheless contains a significant amount of water. The packaged concentrate, containing a plant treatment compound as active ingredient, is shipped to distributors or retailers. Ultimately, the packaged concentrate is purchased by an end user, who dilutes the concentrate by adding water in accordance with label instructions on the package. The fully diluted material is then sprayed on plant foliage.

A significant portion of the cost of such a packaged concentrate is the cost of transporting the concentrate from the manufacturing site to the location where the end user purchases it. Any liquid concentrate formulation that contains relatively less water and thus more active ingredient would reduce the cost per unit amount of active ingredient. However, one important limit on the ability of the manufacturer to increase concentration (ie., "loading") of the active ingredient in a concentrate formulation is the physical stability of that formulation. With some combinations of formulation ingredients, an upper limit to loading of the active ingredient is reached beyond which any further reduction of water content in the concentrate causes physical instability (e.g., separation into discrete layers), which generally makes the concentrate commercially unacceptable.

Until now, the problems presented by such physical instability have been avoided by such expedients as (a) formulating the concentrate in solid rather than liquid form, (b) restricting surfactant choice to the relatively narrow range of surfactants showing good physical compatibility with high ionic strength solutions, or (c) limiting the concentration of a surfactant such as a polyoxyethylene alkylether to a low level, often in combination with a second surfactant or other coformulant that acts as a compatibility agent. Illustrations of such expedients are provided by literature on glyphosate formulations.

It is known to include a relatively high concentration of a polyoxyethylene alkylether surfactant together with a glyphosate salt in a solid formulation. For example, U.S. Pat. No. 4,931,080 discloses a solid powder composition containing the polyoxyethylene alkylether surfactant Plurafac™ A-39 of BASF and glyphosate trimethylsulfonium salt, in a weight ratio of 1:1.64. The weight ratio of surfactant to glyphosate acid equivalent (a.e.) in this composition can be calculated to be about 1:1.13. Two other compositions are disclosed having the same ingredients in an even higher weight ratio of surfactant to glyphosate a.e. (1:0.86 and 1:0.69).

Solid formulations such as those disclosed in above-cited U.S. Pat. No. 4,931,080 have numerous benefits but most end users prefer the convenience of liquid formulations. Further, the compositions of U.S. Pat. No. 4,931,080 containing Plurafac™ A-39 are disclosed therein to be less herbicidally effective than a comparative liquid formulation having a surfactant identified as "Ethoquad 12" (sic; possibly Ethoquad™ 18/12 of Akzo) at a weight ratio of surfactant to glyphosate a.e. of 1:1.71. Thus polyoxyethylene alkylether surfactants such as Plurafac™ A-39 are shown in the art to be relatively weak enhancers of glyphosate herbicidal effectiveness when used at high surfactant to glyphosate a.e. ratios (1:1.13 and higher).

In the art of making aqueous liquid concentrate formulations of salts of glyphosate such as the isopropylammonium and trimethylsulfonium salts, where the formulations contain a substantial quantity of surfactant, cationic surfactants such as polyoxyethylene alkylamines and quaternary ammonium salts, amphoteric surfactants such as polyoxyethylene alkylamine oxides, and a very limited range of nonionic surfactants such as alkyl polyglucosides that exhibit good physical compatibility with high ionic strength solutions, have hitherto been preferred. Where polyoxyethylene alkylether surfactants have been included in an aqueous concentrate formulation of a glyphosate salt, they have generally been present in relatively low concentration and/or as minor components of a blend of surfactants in which more compatible types such as quaternary ammonium salt or alkyl polyglucoside surfactants predominate. Further, the polyoxyethylene alkylethers used in this way have in general been of relatively low molecular weight, having a hydrophobic moiety consisting of a relatively short (e.g., $C_{9-15}$) hydrocarbon chain and/or having a hydrophilic moiety consisting of a relatively short polyoxyethylene chain (e.g., 3–10 oxyethylene units).

Illustrative examples of such formulations can be found in International Patent Publication No. WO 95/16351, wherein the polyoxyethylene alkylether is an ethoxylated secondary alcohol such as Tergitol™ 15-S-9 of Union Carbide, in which the hydrophobic moiety is a $C_{11-15}$ hydrocarbon chain and the hydrophilic moiety is a polyoxyethylene chain having on average about 9 oxyethylene units. In order to provide a stable aqueous concentrate, the polyoxyethylene alkylether surfactant is accompanied by, for example, a cationic surfactant such as polyoxyethylene (2) N-methyl cocoammonium chloride.

Additional illustrative examples can be found in U.S. Pat. No. 5,464,806, wherein the polyoxyethylene alkylether is an ethoxylated acetylenic diol such as Surfynol™ 465 of Air Products, in which the hydrophobic moiety is a branched $C_{14}$ hydrocarbon group that is symmetrical about an acetylenic triple bond and the hydrophilic moiety comprises a pair of polyoxyethylene chains. Various cosurfactants for the ethoxylated acetylenic diol are disclosed that can help provide a stable aqueous concentrate formulation. These include cationic surfactants such as Ethoquad™ C/12W, Ethoquad™ 18125 and Ethomeen™ T/25 of Akzo and Emcol™ CC-9 of Witco, and a nonionic surfactant "APG 325" (Agrimul™ PG 2069 of Henkel).

As indicated above, the prime motivation for including a surfactant in a formulation of a foliar-applied plant treatment compound such as glyphosate is to enhance biological effectiveness of the plant treatment compound. This motivation has often led to the use of relatively large amounts of surfactant in relation to the amount of active ingredient, for example a weight ratio of surfactant to active ingredient of at least about 1:2, in many cases about 1:1 or even higher. An enduring problem in the art is that the more surfactant that has to be included in an aqueous concentrate formulation, the lower is the maximum active ingredient loading that can be achieved.

Co-assigned U.S. patent application Ser. No. 08/957750, the pertinent disclosure of which is incorporated herein by reference, teaches that biological effectiveness of foliar-applied plant treatment compounds or exogenous chemicals, including glyphosate, is enhanced to a surprising degree by inclusion in a composition thereof, at a lower weight ratio of surfactant to glyphosate a.e. than previously disclosed, an alkylether or alkenylether surfactant having formula I:

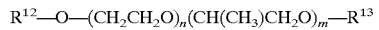
$$R^{12}-O-(CH_2CH_2O)_n(CH(CH_3)CH_2O)_m-R^{13} \qquad I$$

wherein $R^{12}$ is an alkyl or alkenyl group having about 16 to about 22 carbon atoms, n is a number whose average is about 10 to about 100, m is a number of 0 to an average of about 5, and $R^{13}$ is hydrogen or a $C_{1-4}$ alkyl group. The weight ratio of such polyoxyethylene alkylether or alkenylether surfactant to plant treatment compound is about 1:3 to about 1:100. The high degree of herbicidal effectiveness of compositions of U.S. patent application Ser. No. 08/957750 is especially surprising in view of the relatively poor results previously reported for higher weight ratios of surfactant to glyphosate a.e. in above-cited U.S. Pat. No 4,931,080.

Preferably, in a surfactant of formula I, $R^{13}$ is hydrogen and m is 0, thus a preferred class of alkylether or alkenylether surfactants of U.S. patent application Ser. No. 08/957750 has formula II:

$$R^{12}-O-(CH_2CH_2O)_nH \qquad II$$

wherein $R^{12}$ is an alkyl or alkenyl group having about 16 to about 22 carbon atoms and n is a number whose average is about 10 to about 100.

Clearly, from this teaching, it would be desirable to make a highly loaded concentrate formulation of a plant treatment compound and a polyoxyethylene alkylether surfactant wherein the weight ratio of such surfactant to the plant treatment compound is relatively low, for example no higher than about 1:2, or no higher than about 1:3. Such formulations are indeed disclosed in above-cited U.S. patent application Ser. No. 08/957750, but further investigation has shown these formulations to lack the degree of shelf-stability required for commercial acceptability. In particular, they exhibit phase separation when stored for periods of a month or more, in some cases for periods as short as 24 hours, especially under temperature conditions that vary in the range from about −10° C. to about 50° C., as are experienced by agricultural chemical formulations in normal commercial use.

Among the plant treatment compounds whose biological effectiveness is taught by U.S. application Ser. No. 08/957750 to be enhanced are compounds that are acids of relatively low solubility in water, for example below about 50 grams per liter (g/l). Such compounds are almost universally formulated as water-soluble salts. In the case of glyphosate, for example, aqueous compositions are typically prepared using an alkali metal (e.g., sodium or potassium) salt, an ammonium salt, an alkylammonium (e.g., dimethylammonium or isopropylammonium) salt, an alkanolammonium (e.g., monoethanolamine) salt or an alkylsulfonium (e.g., trimethylsulfonium) salt.

The particular instability problem referred to above relates to the fact that surfactants of formula II, when placed in an aqueous solution of high ionic strength, such as a concentrated solution of a plant treatment compound in salt form, tend to separate from the solution so that two discrete phases are formed, one of which consists primarily of the surfactant and one that is primarily aqueous and typically contains most of the dissolved plant treatment compound. In some cases it is possible to disperse such a surfactant, in the presence or absence of an oil such as butyl stearate, in the solution, so that the surfactant remains dispersed for at least a few hours or days at ambient temperature. However, such dispersions are rarely physically stable for prolonged periods, especially over a range of storage temperatures as are typically experienced by commercial agricultural chemical formulations in normal use.

U.S. patent application Ser. No. 08/957750 teaches that greater stability can be imparted to an aqueous concentrate composition containing a dispersed surfactant of formula II and a plant treatment compound in salt form by adding other ingredients, for example colloidal particulate silica or aluminum oxide at 0.5% to 2.5% by weight. Even with such addition, however, experience has shown that physical stability of the aqueous concentrate composition is generally insufficient to provide a commercially acceptable shelf-life.

Thus, a particular problem addressed by the present invention is to prepare a stable, highly loaded aqueous concentrate composition containing a plant treatment compound such as glyphosate and a polyoxyethylene alkylether surfactant, wherein the surfactant is present at a weight ratio to the plant treatment compound of about 1:2 or less, but in an amount sufficient, upon dilution of the composition in water and application of the diluted composition to foliage of a plant, to provide the desired enhancement of biological effectiveness of the plant treatment compound. By "highly loaded" in this context is meant a concentration of active ingredient, expressed as acid equivalent (a.e.), not less than about 240 grams per liter (g a.e./l). More desirably, the concentration of active ingredient is about 300 g a.e./l or higher, ideally as high as, say, 360–480 g a.e./l.

As aqueous concentrate compositions containing a plant treatment compound such as glyphosate and a surfactant typically have densities of about 1.1 to about 1.2 grams per milliliter (g/ml), a "highly loaded" composition as defined above can be calculated to have a concentration of active ingredient not less than about 20% by weight, more desirably about 25% by weight or higher, ideally as high as, say, 30–44% by weight.

International Patent Publication No. WO 94/19941 discloses one approach to solving this problem by which it is implied that a concentration of 5% to 58% by weight of a plant treatment compound (for example glyphosate or glufosinate) can be achieved in an aqueous composition in the presence of any of a variety of surfactants. This approach involves preparing an aqueous suspension of glyphosate or glufosinate herbicide in the presence of a concentrated solution of an electrolyte. The herbicide can be in its acid form or in the form of a salt. Alternatively, both acid and salt forms can be present. The presence of the electrolyte is stated to lower solubility of the suspended herbicide, hence reduce risk of crystal growth and thereby improve long-term stability of the suspension. Experiment no. 26 of WO 94/19941 teaches a suspension concentrate containing 20.4% by weight of glyphosate acid, 10.2% by weight of polyoxyethylene (25) stearylether (a surfactant of formula II above), 27.2% by weight of ammonium sulfate as electrolyte, 1.4% by weight of colloidal attapulgite clay and 40.8% by weight of water. No higher loading than 20.4% by weight is specifically exemplified for glyphosate acid together with a surfactant of formula II. A density of 1.27 g/ml is reported for the composition of Experiment no. 26, from which it can be calculated that the glyphosate loading was about 260 g a.e./l. It is disclosed that following storage at various temperatures, this composition exhibited an "upper clear phase" amounting to 10% of the volume of the composition.

The disclosure that follows provides a new solution for the storage stability problem of a highly loaded aqueous concentrate composition of a plant treatment compound that also contains a polyoxyethylene alkylether or alkenylether surfactant in a desirable weight ratio to the plant treatment compound.

SUMMARY OF THE INVENTION

In the present invention, a polyoxyethylene alkylether or alkenylether surfactant different from those of formulas I and II above is selected for use with a plant treatment compound to provide concentrate compositions, in particular aqueous concentrate compositions, having benefits over compositions known in the art. According to this invention, a particularly advantageous surfactant for use in conjunction with a foliar-applied plant treatment compound has the representative chemical formula III:

$$R-O-(CH_2CH_2O)_n-H \qquad III$$

wherein R is a straight or branched chain aliphatic hydrocarbyl group having about 24 to about 60 carbon atoms in the chain and n is an integer having an average value of about 5 to about 100. The weight ratio of the surfactant to the plant treatment compound is about 1:2 to about 1:30. A surfactant of formula III is especially useful where the plant treatment compound is an acid and is present predominantly in the acid form as defined herein.

In one embodiment of the invention there is therefore provided a liquid or solid concentrate composition suitable, following dilution, dissolution or dispersion of the composition in water, for foliar application to a plant to elicit a biological activity in the plant. This concentrate composition comprises (a) a plant treatment compound that is an acid having a solubility in water at 25° C. of less than about 50 g/l and is present, predominantly in the acid form thereof, in an amount of about 20% to about 90% by weight, expressed as acid equivalent (a.e.), of the composition, and (b) a surfactant of formula III above in a weight ratio to the plant treatment compound, expressed as acid equivalent, of about 1:2 to about 1:30.

The present invention is more particularly drawn to an liquid suspension concentrate composition of a plant treatment compound that is an acid having a solubility in deionized water at 25° C. of less than about 50 g/l, this composition being suitable for foliar application following dilution of the composition in water. A composition of this embodiment of the invention has a continuous aqueous phase and a discontinuous particulate phase, and comprises (a) about 240 to about 540 grams acid equivalent per liter of the plant treatment compound, predominantly in the acid form thereof, (b) a surfactant of formula III above in a weight ratio to the plant treatment compound, expressed as acid equivalent, of about 1:2 to about 1:30, and (c) water. The discontinuous particulate phase is comprised predominantly of the plant treatment compound.

In a further embodiment, the plant treatment compound is a herbicidal compound. Thus, there is provided an aqueous suspension concentrate composition of a herbicide that is an acid having a solubility in deionized water at 25° C. of less than about 50 g/l, this composition being suitable for foliar application following dilution of the composition in water. A composition of this embodiment of the invention has a continuous aqueous phase and a discontinuous particulate phase, and comprises (a) about 240 to about 540 grams acid equivalent per liter of the herbicidal compound, predominantly in the acid form thereof, (b) a surfactant of formula III above in a weight ratio to the plant treatment compound, expressed as acid equivalent, of about 1:2 to about 1:30, and (c) water. The discontinuous particulate phase is comprised predominantly of the herbicidal compound.

A preferred herbicidal compound is N-phosphonomethylglycine (glyphosate). Thus, there is provided an aqueous suspension concentrate herbicidal composition of N-phosphonomethylglycine suitable for foliar application following dilution in water. Such a composition has a continuous aqueous phase and a discontinuous particulate phase, and comprises (a) about 240 to about 540 grams acid equivalent per liter of N-phosphonomethylglycine, predominantly in the acid form thereof, (b) a surfactant of formula III above in a weight ratio to the N-phosphonomethylglycine, expressed as acid equivalent, of about 1:2 to about 1:30, and (c) water. The discontinuous particulate phase is comprised predominantly of the N-phosphonomethylglycine.

Also provided is a method of killing or controlling unwanted vegetation comprising diluting in a suitable volume of water a herbicidally effective amount of an aqueous suspension concentrate composition of a herbicidal compound as provided herein to make a spray composition, and applying the spray composition by spraying to foliage of the unwanted vegetation.

A salient benefit of this invention is that compositions of the invention provide a high degree of biological effectiveness. The invention, in addition to providing a subclass of polyoxyethylene alkylether and alkenylether surfactants not hitherto specifically known to be useful in enhancement of biological effectiveness of foliar-applied plant treatment compounds such as herbicides, provides a new solution to the storage-stability problems of aqueous concentrate compositions containing polyoxyethylene alkylether or alkenylether surfactants previously disclosed. Still further benefits and advantages will be apparent to those skilled in the art from the disclosure herein.

DETAILED DESCRIPTION OF THE INVENTION

Nature of Contemplated Compositions

According to the present invention, surfactants of formula III above give unexpectedly strong enhancement of biological effectiveness of foliar-applied plant treatment compounds. This finding is independent of the chemical form in which a plant treatment compound is present in a composition. Thus, for example, a plant treatment compound that can exist as an acid or as a derivative, including but not restricted to a salt or an ester, thereof, can usefully be formulated with a surfactant of formula III in any of the acid or derivative forms of the plant treatment compound, so long as the acid or derivative form selected is biologically active.

It is contemplated that any composition of a plant treatment compound or exogenous chemical embraced by the disclosure of above-cited U.S. patent application Ser. No. 08/957750, and containing a surfactant of formula I or formula II, can be usefully modified by substituting a surfactant of formula III as provided herein for the surfactant of formula I or formula II.

However, the advantages of the present invention are particularly marked when the plant treatment compound is an acid having a solubility in deionized water at 25° C. of less than about 50 g/l, and is present predominantly in the acid form. Preferred acids are those having a carboxylic acid or phosphonic acid moiety, or both. It is further preferred that the acid have a solubility in water at 25° C. of less than about 20 g/l.

The expression "predominantly in the acid form" as used herein means that for each mole of the plant treatment compound present, less than about 0.5 mole of protons can have been donated from the plant treatment compound to salt-forming bases. That is to say, salt-forming cations (ie., cations other than hydrogen ions, or protons) present in the composition have positive charges that are in total equivalent to less than about 0.5 mole of protons per mole of the plant treatment compound. Thus, for example, in a composition containing one mole of a plant treatment compound that is an acid, together with less than 0.5 mole of monovalent salt-forming cations such as ammonium or sodium ions, or less than 0.25 mole of divalent salt-forming cations such as magnesium ions, the plant treatment compound is "predominantly in the acid form" as herein defined.

In an important embodiment of the invention, the composition is an aqueous suspension concentrate composition having a discontinuous particulate phase and a continuous aqueous phase. The discontinuous particulate phase is comprised predominantly of the plant treatment compound (i.e., at least about 50% by weight of the particulate phase is accounted for by the plant treatment compound). If salt-forming cations are present, they may form a salt or salts with some of the plant treatment compound, and such salt or salts can exist either in the discontinuous particulate phase or in the continuous aqueous phase. However, of that portion of the plant treatment compound which is present in its acid form, most is in the discontinuous particulate phase.

In order to assay the content of the plant treatment compound in the discontinuous particulate phase, any technique known in the art for separating this phase from the continuous aqueous phase can be employed. For example, filtration or centrifugation techniques are useful.

In a preferred embodiment, no substantial amount of salt-forming cations is present in the composition. It will be recognized, however, that the presence of a minor amount of one or more salt-forming cations, such as can be introduced for example in normal water, is consistent with this preferred embodiment of the invention. Thus the phrase "no substantial amount" as used herein with reference to the presence of salt-forming cations can be understood, for example, as meaning less than about 0.1 mole in total of such cations per mole of the plant treatment compound.

In this respect a composition of this embodiment of the invention differs from compositions made using a plant treatment compound in the form of a salt thereof, as exemplified by the glyphosate salt compositions containing polyoxyethylene alkylether or alkenylether surfactants disclosed in U.S. patent application Ser. No. 08/957750 cited above. In an aqueous concentrate composition having the plant treatment compound in salt form, the plant treatment compound is typically present predominantly in the continuous aqueous phase, where the ionic strength contributed by the plant treatment compound is believed to "salt out" the surfactant. Thus, in such a composition the surfactant tends to exist in a separate phase from the continuous aqueous phase, either in a discrete layer or forming a stable or unstable dispersion of surfactant-containing particles. By contrast, in an aqueous suspension concentrate composition of the present invention containing the plant treatment compound in acid form, it is believed that only a small amount of the plant treatment compound is typically dissolved in the aqueous phase and the surfactant is not "salted out". In other words, it is believed that the distribution of plant treatment compound and surfactant between continuous and discontinuous phases of such a composition is reversed by comparison with the compositions disclosed in U.S. patent application Ser. No. 08/957750.

Plant Treatment Compound

Examples of foliar-applied plant treatment compounds that can be included in compositions of the present invention include, but are not limited to, chemical pesticides (such as herbicides, algicides, fungicides, bactericides, viricides, insecticides, aphicides, miticides, nematicides, molluscicides and the like), plant growth regulators, fertilizers and nutrients, gametocides, defoliants, desiccants, mixtures thereof and the like. A "foliar-applied" plant treatment compound as defined herein is one that is normally applied post-emergence to foliage of plants.

Preferred plant treatment compounds for use in compositions of the present invention are herbicides, plant growth regulators and nematicides.

Herbicides that are acids useful in compositions of the invention include without restriction acifluorfen, asulam, benazolin, bentazon, bialaphos, bispyribac, bromacil, bromoxynil, chloramben, clopyralid, 2,4-D, 2,4-DB, dalapon, dicamba, dichlorprop, diclofop, endothall, fenac, fenoxaprop, flamprop, fluazifop, fluoroglycofen, fluroxypyr, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, sulfamic acid, 2,3,6-TBA, TCA and triclopyr.

Plant growth regulators that are acids useful in compositions of the invention include without restriction ethephon, gibberellic acid, glyphosine, maleic hydrazide, mefluidide, NAA and TIBA.

Nematicides that are acids useful in compositions of the invention include without restriction those disclosed in U.S. Pat. No. 5,389,680, the pertinent disclosure of which is incorporated herein by reference. Preferred nematicides of this group are 3,4,4-trifluoro-3-butenoic acid and N-(3,4,4-trifluoro-1-oxo-3-butenyl)glycine.

More than one plant treatment compound that is an acid can, if desired, be used in a single composition of the invention. For example, an aqueous suspension concentrate composition can be made having both glyphosate and dicamba acids. In such a case, features such as concentration ranges disclosed herein as applying to a single plant treatment compound are to be understood as applying to the total of all plant treatment compounds present. Similarly, the ranges of weight ratio of surfactant to plant treatment compound disclosed herein are to be understood as applying to the weight ratio of surfactant to the total of all plant treatment compounds present, when a plurality of plant treatment compounds that are acids are included in a single composition.

Thus, for example, an aqueous suspension concentrate composition containing glyphosate predominantly in the acid form thereof at a concentration of 180 g a.e./l, and dicamba predominantly in the acid form thereof at a concentration of 90 g a.e./l, together with a surfactant of formula III at a concentration of 80 g a.e./l, is embraced by the present invention, provided that other conditions recited herein are met.

The present invention is particularly directed to aqueous suspension concentrate formulations of N-phosphonomethylglycine, or glyphosate. The herbicidal properties of N-phosphonomethylglycine and its derivatives were first discovered by Franz, then disclosed and patented in U.S. Pat. No. 3,799,758, issued Mar. 26, 1974, the pertinent disclosure of which is incorporated herein by reference.

N-phosphonomethylglycine has three acid sites, thus salts can be made having up to 3 moles in total of monovalent salt-forming cations, or up to 1.5 moles in total of divalent salt-forming cations, per mole of N-phosphonomethylglycine. In a preferred embodiment of the invention, however, N-phosphonomethylglycine is present predominantly in the acid form thereof. Salt-forming cations present in a contemplated formulation can result in some of the N-phosphonomethylglycine being present as one or more salts. Such a result is consistent with this embodiment of the invention provided that for each mole of N-phosphonomethylglycine present, salt-forming cations present have positive charges that are in total equivalent to less than about 0.5 mole of protons.

Whether the plant treatment compound is glyphosate, another compound, or a mixture of two or more compounds, the concentration, or loading, of plant treatment compound (s) in total is at least about 240 g a.e./l, preferably at least about 300 g a.e./l, and more preferably at least about 360 g a.e./l. For practical purposes the maximum loading in a suspension concentrate of glyphosate acid of the invention is about 540 g a.e./l. Loadings above this level can be achieved only by reducing the amount of surfactant to a level that is unlikely to give the desired biological effectiveness, and the resulting formulation, besides having relatively weak biological effectiveness, tends to suffer handling problems such as those attendant upon high viscosity. An especially preferred loading of plant treatment compound(s) in total is about 360 to about 480 g a.e./l.

Plant treatment compounds are applied to plants at a rate sufficient to give the desired effect. An application rate is usually expressed as an amount of compound per unit area treated, e.g., grams per hectare (g/ha). What constitutes a "desired effect" varies according to the standards and practice of those who investigate, develop, market and use a specific class of plant treatment compounds or formulations thereof. For example, in the case of a herbicide, the amount applied per unit area to give 85% control of a plant species as measured by growth reduction or mortality is often used to define a commercially effective rate.

"Herbicidal effectiveness" as used herein refers to any observable measure of control of plant growth, which can include one or more of the actions of (1) killing, (2) inhibiting growth, reproduction or proliferation, and (3) removing, destroying, or otherwise diminishing the occurrence and activity of plants.

Herbicidal effectiveness data typically report "inhibition" or "control" as a percentage following a standard procedure in the art which reflects a visual assessment of plant mortality and growth reduction by comparison with untreated plants, made by technicians specially trained to make and record such observations. A single technician preferably makes all assessments of percent inhibition within any one experiment or trial. Such assessments are relied upon and regularly reported by Monsanto Company in the course of its herbicide business.

The selection of application rates that are biologically effective for a specific plant treatment compound is within the skill of the ordinary agricultural scientist. Those of skill in the art will likewise recognize that individual plant conditions, weather and growing conditions, as well as the specific plant treatment compound and formulation thereof selected, affect the biological effectiveness that can be achieved in practicing this invention. Useful application rates for plant treatment compounds employed can depend upon all of the above conditions. With respect to the use of a method of this invention employing a herbicidal composition of glyphosate, much information is known that can help select appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for control of which glyphosate compositions are used are exemplified without limitation by velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.).

Particularly important annual narrowleaf weed species for control of which glyphosate compositions are used are exemplified without limitation by wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for control of which glyphosate compositions are used are exemplified without limitation by mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for control of which glyphosate compositions are used are exemplified without limitation by brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other important perennial species for control of which glyphosate compositions are useful are exemplified without limitation by horsetail (Equisetum spp.), bracken (*Pteridium aquilinum*), blackberry (Rubus spp.) and gorse (*Ulex europaeus*).

Thus a composition of the present invention, as it pertains to glyphosate herbicide, can be useful on any of the above species. It is contemplated that on one or more of the above species, a composition of the present invention provides enhanced herbicidal effectiveness by comparison with standard (e.g., commercial) formulations of glyphosate of similar a.e. loading known in the art, when applied at equal glyphosate a.e. rates. It is rer contemplated atht on one or more of the above species, a composition of the present invention provides equal herbicidal effectiveness to a standard formulation of glyphosate of simcilar a.e. loading known in the art, when applied at a reduced glyphosate a.e. rate by comparison with the standard formulation.

Surfactant

Compositions of the present invention include one or more long-chain alkylether or alkenylether surfactants having formula III above. R in formula III is an aliphatic hydrocarbyl group that can be a branched or unbranched, saturated or unsaturated chain having about 24 to about 60 carbon atoms. In commercial preparations of surfactants of formula III, the number of carbon atoms in the chain typically varies within a range, and with respect to such preparations the designation herein of "R" relates to the prevalent molecular species present. Preferably R is a linear saturated alkyl chain having 26 to 50 carbon atoms.

Surfactants of formula III have a polyoxyethylene chain, in which the average number of oxyethylene units is represented in formula III by n. The average value n is about 5 to about 100, preferably about 10 to about 40, and most preferably about 10 to about 20.

Commercial preparations of surfactants useful in the present invention include those sold as Unithox™ surfactants by Petrolite Corporation of Tulsa, Okla. Surfactants useful in compositions of the invention are exemplified by the following products from the Unithox™ range:

Unithox™ 350: R=$C_{26}$ linear alkyl; n=8.
Unithox™ 450: R=$C_{30}$ linear alkyl; n=10.5.
Unithox™ 480: R=$C_{30}$ linear alkyl; n=42.
Unithox™ 490: R=$C_{30}$ linear alkyl; n=94.
Unithox™ 750: R=$C_{50}$ linear alkyl; n=17.

Of the above, Unithox™ 450 and Unithox™ 750 are particularly useful examples.

In a contemplated composition, the weight ratio of surfactant to plant treatment compound is about 1:2 to about 1:30. For best biological effectiveness, it is believed that the weight ratio should be as high as possible in this range, for example about 1:2 to about 1:6. On the other hand, to achieve a high loading of the plant treatment compound in the composition it is generally preferable to have a weight ratio of surfactant to plant treatment compound of about 1:3 to about 1:30. The weight ratio can be selected from within the ranges disclosed herein by routine experimentation and will often be a compromise between the above requirements.

A solid composition consisting essentially of a plant treatment compound and a surfactant of formula III contains about 75% to about 97%, preferably about 75% to about 86%, of the plant treatment compound (including impurities normally present therein), with the balance being surfactant.

In the case of an aqueous suspension concentrate composition of the invention having N-phosphonomethylglycine in its acid form as the plant treatment compound, loadings of up to about 480 g a.e./l of N-phosphonomethylglycine or higher have been achieved with a weight ratio of surfactant to N-phosphonomethylglycine of about 1:3 to about 1:4.5. An illustrative composition of this type has a density of approximately 1.1 g/ml and contains 33% by weight of N-phosphonomethylglycine in the acid form thereof, 10% by weight of Unithox™ 450 or Unithox™ 750 and 57% by weight of water. Another illustrative composition contains 44% by weight of N-phosphonomethylglycine in the acid form thereof, 10% by weight of Unithox™ 450 or Unithox™ 750 and 46% by weight of water.

Aqueous suspensions containing surfactants of formula III unexpectedly show superior storage stability, resistance to sedimentation of the particulate phase and resistance to separation of a surfactant-containing phase, by comparison with similar suspensions containing shorter-chain surfactants such as those of formula II. At the same time, biological effectiveness is substantially maintained.

Surfactants of formula III have rarely been used in formulating plant treatment compounds. U.S. Pat. No. 5,100,667 discloses a process for pelletizing a phosphoroamidothioate or phosphoroamidodithioate insecticide that employs a surfactant exemplified by Unithox™ 480 or Unithox™ 520. U.S. Pat. No. 5,075,058 discloses that such a surfactant is useful in pelletizing a phosphoroamidothioate or phosphoroamidodithioate insecticide in combination with a herbicide, fungicide, fertilizer or other insecticide.

Other Formulation Ingredients

The amount of water present in a composition of the invention is generally determined by difference, e.g., as a weight percentage by subtracting the total weight percentage of all other ingredients from 100%.

Other than water, no additional formulation ingredients beyond those specified above are necessary for practice of the present invention. However, certain improvements in stability or handling properties of aqueous suspension concentrate formulations of the invention have been observed with addition of long-chain fatty alcohols, glycols and/or colloidal particulates.

Addition of a long-chain hydrocarbyl alcohol at about 1% to about 5% by weight has been found to improve physical stability of an aqueous suspension concentrate composition containing N-phosphonomethylglycine in acid form and a surfactant of formula III. An increase in viscosity tends to accompany the improvement in stability. Long-chain alcohols useful in compositions of the invention include, without restriction, those having a linear saturated hydrocarbyl chain matching that of the surfactant used. These are available, for example, as Unilin™ alcohols from Petrolite Corporation. Unilin™ 350 has predominantly a $C_{26}$ linear alkyl chain, matching that of Unithox™ 350. Unilin™ 425 has predominantly a $C_{30}$ linear alkyl chain, matching that of Unithox™ 450, Unithox™ 480 and Unithox™ 490. Unilin™ 700 has predominantly a $C_{50}$ linear alkyl chain, matching that of Unithox™ 750.

Addition of a glycol, for example propylene glycol, at about 1% by weight has been found to improve handling properties of an aqueous suspension concentrate composition containing N-phosphonomethylglycine in acid form and a surfactant of formula III, by lowering viscosity.

Addition of a small amount of a colloidal particulate to an aqueous suspension concentrate composition containing N-phosphonomethylglycine in acid form and a surfactant of formula III has been found in some cases to improve physical stability. Oxides of silicon, aluminum and titanium are preferred colloidal particulate materials. Particle size is preferably such that specific surface area is in the range from about 50 to about 400 $m^2/g$, as reported by the supplier or manufacturer of such materials. An especially useful improvement in storage stability can be obtained using colloidal particulates having a reported specific surface area between about 180 and about 500 $m^2/g$. An example of a particularly useful colloidal particulate is a colloidal silica product sold by Degussa as Aerosil™ 380.

Although various compositions of the present invention are described herein as comprising certain listed materials, in some preferred embodiments of the invention the compositions consist essentially of the indicated materials.

Optionally, other agriculturally acceptable materials can be included in the compositions. For example, more than one plant treatment compound can be included. Also, various agriculturally acceptable adjuvants can be included, whether or not their purpose is to directly contribute to the effect of the plant treatment compound on or in a plant. For example, one or more additional surfactants can be included. Surfactants mentioned here by trade name, and other surfactants that can be useful in the method of the invention, are indexed in standard reference works such as McCutcheon's Emulsifiers and Detergents, 1997 edition, Handbook of Industrial Surfactants, 2nd Edition, 1997, published by Gower, and International Cosmetic Ingredient Dictionary, 6th Edition, 1995.

Process for Preparing Aqueous Suspension Concentrates

Aqueous suspension concentrate compositions in accordance with the present invention can be prepared by the following general process. However, it should be noted that the invention is not limited to compositions made by processes described herein, and that any aqueous suspension concentrate showing acceptable physical stability and having the ingredients disclosed herein in the disclosed amounts is embraced by the present invention regardless of how the concentrate is prepared.

A solid plant treatment compound in acid form is milled if necessary to make a powder. As is well known in the art, particles of small size tend to provide improved suspension stability by comparison with larger particles. For the present purpose, particle size should be no greater than about 30 $\mu$m, preferably no greater than about 20 $\mu$m, and most preferably no greater than about 10 $\mu$m. Air-milling is a suitable method of achieving particle sizes of about 1 $\mu$m to about 10 $\mu$m.

The required weight of a solid surfactant of formula III is heated in a suitable vessel with a stirring device until the surfactant melts. If a fatty alcohol and/or glycol are to be included in the composition, these are preferably added to the surfactant in the desired weight ratio before melting. The melting point of a surfactant of formula III ranges from about 80° C. to about 120° C. depending on hydrocarbyl and polyoxyethylene chain lengths.

Water is heated to a temperature above about 95° C. and the required amount of hot water, measured by weight, is then transferred to a separate mixing vessel. For a laboratory scale preparation, a Waring™ blender has been found useful. If a colloidal particulate is to be included in the composition, the desired weight of the colloidal particulate is added to the hot water in the mixing vessel.

The required weight of powdered plant treatment compound is added to the vessel containing the molten surfactant, where it is rapidly blended into the surfactant to ensure that all of the powder is coated by surfactant. It is important in this process that the temperature of the molten surfactant be below the melting or decomposition point of the plant treatment compound, so that the latter remains particulate and chemically unchanged. The blend of powdered plant treatment compound and molten surfactant can be cooled and milled or granulated by any technique known in the art to make a solid composition; however, in making an aqueous suspension concentrate the blend of powdered plant treatment compound and molten surfactant is quickly added to the mixing vessel containing the hot water. The resulting mixture is blended under low shear to form a suspension while being permitted to cool to ambient temperature or slightly above ambient temperature.

The suspension is then transferred to a suitable container for storage and future use.

Application of Composition to Plants

Compositions of the present invention are diluted in water and then applied, preferably by spraying, to foliage of plants. The composition at the time of application to plants is preferably dilute enough to be readily sprayed using standard agricultural spray equipment. Preferred application rates of a diluted composition of the present invention vary depending upon a number of factors, including the type and concentration of active ingredient and the plant species involved. Useful rates for applying a diluted composition to a field can range from about 25 to about 1,000 liters per hectare (l/ha) by spray application. Preferred application rates are about 50 to about 300 l/ha. Those of skill in the art will recognize that application rate (or "spray volume" as it is conventionally called) can be controlled though a number of parameters, including nozzle configuration and orifice size, spray pressure and forward speed of the spraying device.

The required degree of dilution for preparation of a spray composition in a spray tank can be calculated from the equation $$A = RS/VC$$

where A is the volume in liters (l) of the concentrate composition to be added to the spray tank, R is the desired rate of plant treatment compound to be applied in grams acid equivalent per hectare (g a.e./ha), S is the total volume in liters (l) of spray composition being prepared, V is the application rate in liters per hectare (l/ha) of the spray composition, conventionally referred to as "spray volume", and C is the concentration of plant treatment compound in grams acid equivalent per liter (g a.e./l) in the concentrate composition.

Any conventional means for spraying liquids, such as spray nozzles, atomizers, or the like, can be used for application of diluted compositions. A composition of the present invention, when appropriately diluted, can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply different desired amounts of a diluted composition to different parts of a field.

Many plant treatment compounds (including glyphosate herbicide) must be taken up by living tissues of the plant and translocated within the plant in order to produce the desired biological (e.g., herbicidal) effect. Thus, it is important that a composition containing a translocated compound not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

EXAMPLES

The following Examples are provided for illustrative purposes only and are not intended to limit the scope of the invention.

Example 1

Aqueous suspension concentrate compositions of glyphosate acid were prepared by the procedure described below. All contained 30% by weight glyphosate acid and 10% by weight of a long-chain alkylether surfactant, selected from Unithox™ 350, Unithox™ 450, Unithox™ 480, Unithox™ 490 and Unithox™ 750. Some compositions additionally contained 1% or 5% by weight of a long-chain alcohol, selected from Unilin™ 350, Unilin™ 425 and Unilin™ 750. In all compositions the balance to 100% by weight was water.

Dried technical grade glyphosate acid powder having a mean particle size of about 20 $\mu$m, in an amount of 30.15 g, was weighed into a first beaker. The selected alkylether surfactant, in an amount of 10 g, was melted in a second beaker on a hot plate at heat level 3, with stirring by means of a magnetic stirrer. If a long-chain alcohol was also used, it was added in an appropriate amount (1 or 5 g) to the alkylether surfactant before melting. Deionized water was heated in a microwave oven until boiling or at a temperature >95° C., and the required amount of this hot water (100 g less the weight of the other ingredients mentioned above), determined by weighing in a tared beaker, was quickly transferred to a Waring™ blender cup. The pre-weighed glyphosate acid in the first beaker was transferred to the second beaker containing the molten surfactant, after removal of the magnetic stirrer from the second beaker. The glyphosate acid was rapidly blended into the molten surfactant using a metal spatula to ensure that the acid particles were uniformly coated with surfactant. The blend of glyphosate acid and surfactant was then quickly added to the blender cup containing the pre-weighed hot water. The resulting mixture was blended at the slowest speed setting on the blender to form a suspension, this blending continuing until the suspension had cooled to near room temperature. Finally, the suspension was transferred to a 200 ml clear plastic jar for determination of storage stability.

As indicia of inadequate storage stability, in this and following Examples, "phase separation" refers to the formation of a separate surfactant-containing phase, and "sedimentation" refers to settling of the particulate phase of the composition.

Composition of each of concentrates 1-A to 1-K prepared as above is shown in Table 1.1.

TABLE 1.1

| Concentrate no. | Glyphosate acid weight % | Unithox ™ surfactant | | Unilin ™ alcohol | | Water weight % |
| --- | --- | --- | --- | --- | --- | --- |
| | | type | weight % | type | weight % | |
| 1-A | 30.15 | 350 | 10.00 | 350 | 5.00 | 54.85 |
| 1-B | 30.15 | 450 | 10.00 | 425 | 5.00 | 54.85 |
| 1-C | 30.15 | 350 | 10.00 | 350 | 1.00 | 58.85 |
| 1-D | 30.15 | 450 | 10.00 | 425 | 1.00 | 58.85 |
| 1-E | 30.15 | 480 | 10.00 | 425 | 1.00 | 58.85 |
| 1-F | 30.15 | 490 | 10.00 | 425 | 1.00 | 58.85 |
| 1-G | 30.15 | 750 | 10.00 | 700 | 1.00 | 58.85 |
| 1-H | 30.15 | 350 | 10.00 | none | | 59.85 |
| 1-I | 30.15 | 450 | 10.00 | none | | 59.85 |
| 1-J | 30.15 | 490 | 10.00 | none | | 59.85 |
| 1-K | 30.15 | 750 | 10.00 | none | | 59.85 |

The following observations were made after storage for 24 hours (Table 1.2) and 6 days (Table 1.3) at room temperature.

TABLE 1.2

| Concentrate no. | Observation after 24 h at room temperature |
|---|---|
| 1-A | gelled, no phase separation, no sedimentation |
| 1-B | no phase separation, no sedimentation |
| 1-C | phase separation, sedimentation |
| 1-D | no phase separation, no sedimentation |
| 1-E | no phase separation, no sedimentation |
| 1-F | no phase separation, no sedimentation |
| 1-G | phase separation (yellowish top layer), no sedimentation |
| 1-H | phase separation, sedimentation |
| 1-I | relatively non-viscous, no phase separation, no sedimentation |
| 1-J | phase separation (foam-like top layer), no sedimentation |
| 1-K | relatively non-viscous, no phase separation, no sedimentation |

TABLE 1.3

| Concentrate no. | Observation after 6 days at room temperature |
|---|---|
| 1-A | too viscous to flow, no phase separation |
| 1-B | very viscous, no phase separation |
| 1-C | bottom clearing, 5% of volume |
| 1-D | very viscous, no phase separation |
| 1-E | no phase separation |
| 1-F | moderately viscous, no phase separation |
| 1-G | top clearing, 5% of volume |
| 1-H | bottom clearing, 10% of volume |
| 1-I | relatively non-viscous, no phase separation |
| 1-J | top clearing, 5% of volume |
| 1-K | relatively non-viscous, no phase separation |

About 5 ml of some of the above compositions were transferred to small glass vials and placed in an oven at 50° C. Observations following this high temperature exposure are shown in Tables 1.4 and 1.5.

TABLE 1.4

| Concentrate no. | Observation after storage for 18 h at 50° C. |
|---|---|
| 1-D | too viscous to flow, no phase separation, large amount of entrapped air |
| 1-E | too viscous to flow, no phase separation, small amount of entrapped air |
| 1-I | relatively non-viscous, top clearing, <5% of volume |
| 1-K | relatively non-viscous, no phase separation |

TABLE 1.5

| Concentrate no. | Observation after storage for 7 days at 50° C. |
|---|---|
| 1-D | too viscous to flow, foamy solid at top |
| 1-E | too viscous to flow, bottom clearing, 10% of volume |
| 1-I | relatively non-viscous, top clearing, 20% of volume |
| 1-K | relatively non-viscous, top clearing, 10% of volume |

It was concluded from the stability studies of Example 1 that alkylether surfactants having a relatively low degree of ethoxylation (e.g., Unithox™ 450) provide better physical stability to aqueous suspension concentrate formulations of glyphosate acid than alkylether surfactants with a higher degree of ethoxylation (e.g., Unithox™ 490). Addition of long-chain alcohol tended to improve physical stability but dramatically increased viscosity. The most acceptably stable and non-viscous compositions in this study were those made with Unithox™ 450 or Unithox™ 750.

Example 2

Aqueous suspension concentrate compositions of glyphosate acid were prepared by the procedure described below. All contained 30% by weight glyphosate acid and 10% by weight Unithox™ 480. Various additives were included at 5% or 1% by weight as shown in Table 2.1. In all compositions the balance to 100% by weight was water.

Dried technical grade glyphosate acid powder having a mean particle size of about 20 μm, in an amount of 30.15 g, was weighed into a first beaker. Unithox™ 480, in an amount of 10 g, was melted in a second beaker on a hot plate at heat level 2, with stirring by means of a magnetic stirrer. The desired additive, if present, was weighed into a third beaker. Deionized water was heated in a microwave oven until boiling or at a temperature >95° C., and the required amount of this hot water (100 g less the weight of the other ingredients mentioned above), was quickly transferred to the third beaker containing the pre-weighed additive. After stirring rapidly with a metal spatula, the mixture of hot water and additive was transferred to a Waring™ blender cup. The pre-weighed glyphosate acid in the first beaker was transferred to the second beaker containing the molten surfactant, after removal of the magnetic stirrer from the second beaker. The glyphosate acid was rapidly blended into the molten surfactant using a metal spatula to ensure that the acid particles were uniformly coated with surfactant. The blend of glyphosate acid and surfactant was then quickly added to the blender cup containing the pre-weighed hot water/additive mixture. The resulting mixture was blended at the slowest speed setting on the blender to form a suspension, this blending continuing until the suspension had cooled to near room temperature. Finally, the suspension was transferred to a 200 ml clear plastic jar for determination of storage stability.

An exception to the above procedure was for concentrate 2-H, where the additive was sulfuric acid. Sulfuric acid was added very slowly to the hot water in a fume hood.

Composition of each of concentrates 2-A to 2-D and 2-F to 2-R prepared as above is shown in Table 2.1. There was no concentrate 2-E.

TABLE 2.1

| Concentrate no. | Glyphosate acid wt % | Unithox™ 480 wt % | Additive type | wt % | Water wt % |
|---|---|---|---|---|---|
| 2-A | 30.15 | 10.00 | sodium caprylate | 5.00 | 54.85 |
| 2-B | 30.15 | 10.00 | tetraethylammonium bromide | 5.00 | 54.85 |
| 2-C | 30.15 | 10.00 | sodium salicylate | 5.00 | 54.85 |
| 2-D | 30.15 | 10.00 | urea | 5.00 | 54.85 |
| 2-F | 30.15 | 10.00 | polyethylene glycol, MW 400 | 5.00 | 54.85 |
| 2-G | 30.15 | 10.00 | dipropylene glycol | 5.00 | 54.85 |
| 2-H | 30.15 | 10.00 | sulfuric acid | 5.00 | 54.85 |
| 2-I | 30.15 | 10.00 | magnesium sulfate | 5.00 | 54.85 |
| 2-J | 30.15 | 10.00 | sodium sulfate | 5.00 | 54.85 |
| 2-K | 30.15 | 10.00 | trisodium citrate | 5.00 | 54.85 |
| 2-L | 30.15 | 10.00 | disodium hydrogen phosphate | 5.00 | 54.85 |
| 2-M | 30.15 | 10.00 | tetrabutylammonium sulfate | 5.00 | 54.85 |
| 2-N | 30.15 | 10.00 | tetramethylammonium iodide | 5.00 | 54.85 |

TABLE 2.1-continued

| Concentrate no. | Glyphosate acid wt % | Unithox ™ 480 wt % | Additive type | wt % | Water wt % |
|---|---|---|---|---|---|
| 2-O | 30.15 | 10.00 | sodium iodide | 5.00 | 54.85 |
| 2-P | 30.15 | 10.00 | stearyl alcohol | 5.00 | 54.85 |
| 2-Q | 30.15 | 10.00 | Aerosil ™ 380 | 1.00 | 58.85 |
| 2-R | 30.15 | 10.00 | none | | 59.85 |

The following observations were made after storage for 24 hours at room temperature (Table 2.2).

TABLE 2.2

| Concentrate no. | Observation after 24 h at room temperature |
|---|---|
| 2-A | top clearing, 10% of volume, no sedimentation |
| 2-B | top clearing, amber color, 25% of volume, sedimentation |
| 2-C | top clearing, amber color, 33% of volume, sedimentation |
| 2-D | no phase separation, no sedimentation |
| 2-F | top clearing, 25% of volume, sedimentation |
| 2-G | no phase separation, no sedimentation |
| 2-H | no phase separation, sedimentation |
| 2-I | viscous paste, no phase separation, sedimentation |
| 2-J | top clearing, amber color, 50% of volume, sedimentation |
| 2-K | large amount of entrapped air, no sedimentation |
| 2-L | top clearing, 25% of volume, sedimentation |
| 2-M | top clearing, yellow color, 25% of volume, sedimentation |
| 2-N | entrapped air, no phase separation, no sedimentation |
| 2-O | entrapped air, no phase separation, no sedimentation |
| 2-P | entrapped air, no phase separation, no sedimentation |
| 2-Q | entrapped air, no phase separation, no sedimentation |
| 2-R | entrapped air, no phase separation, sedimentation |

It was concluded from the stability studies of Example 2 that physical stability of aqueous concentrate formulations of glyphosate acid with Unithox™ 480 can be improved by addition of a small amount of various additives including urea, dipropylene glycol, stearyl alcohol and Aerosil™ 380.

Example 3

Aqueous concentrate compositions of glyphosate were prepared by the procedures described below. All contained 10% by weight of an alkylether surfactant, Unithox™ 480, Unithox™ 750 or polyoxyethylene (30) stearylether (STA-30 of Heterene). Unilin™ 425 or Aerosil™ 380 at 1% by weight was included in some compositions as shown in Table 3.1. Glyphosate was present in the acid form, or in the form of the isopropylamine (IPA) salt, or as a mixture of both forms, in a total amount of 31% or 44% acid equivalent by weight. In all compositions the balance to 100% by weight was water.

Aqueous suspension concentrate compositions of glyphosate acid were prepared substantially as described for Example 2. For compositions containing IPA salt of glyphosate as well as glyphosate acid, the IPA salt was supplied as a 62% by weight (45% by weight acid equivalent) aqueous solution having a pH of 4.4 to 4.6. IPA salt solution was added in the required amount to the water before heating.

Compositions containing IPA salt of glyphosate but no glyphosate acid were prepared by the following procedure. The required amount of colloidal particulate (in this case Aerosil™ 380) was suspended in a 62% by weight aqueous solution of IPA salt of glyphosate and agitated to make a homogeneous mixture. The required amount of deionized water was added to the mixture, which was then heated in a microwave oven to 60° C. The warm mixture was transferred to a Waring™ blender cup. While blending at the lowest speed setting on the blender, the required amount of surfactant, previously melted as indicated in Example 2, was added. Blending continued until the mixture had cooled to near room temperature.

Composition of each of concentrates 3-A to 3-I is shown in Table 3.1.

TABLE 3.1

| Concentrate no. | Glyphosate weight % a.e. as acid | Glyphosate weight % a.e. as IPA salt | Surfactant type | Surfactant weight % | Additive type | Additive weight % | Water weight % |
|---|---|---|---|---|---|---|---|
| 3-A | 30.61 | | Unithox ™ 480 | 10.00 | Unilin ™ 425 | 1.00 | 58.39 |
| 3-B | | 30.50 | Unithox ™ 480 | 10.00 | Aerosil ™ 380 | 1.00 | 20.00* |
| 3-C | 30.61 | | Unithox ™ 480 | 10.00 | Aerosil ™ 380 | 1.00 | 58.39 |
| 3-D | 30.61 | | STA-30 | 10.00 | Aerosil ™ 380 | 1.00 | 58.39 |
| 3-E | 30.61 | | Unithox ™ 750 | 10.00 | Aerosil ™ 380 | 1.00 | 58.39 |
| 3-F | 30.61 | | Unithox ™ 750 | 10.00 | none | | 59.39 |
| 3-G | 22.00 | 22.00 | Unithox ™ 750 | 10.00 | none | | 18.23* |
| 3-H | 44.00 | | Unithox ™ 750 | 10.00 | none | | 46.00 |
| 3-I | 13.20 | 17.58 | Unithox ™ 750 | 10.00 | none | | 37.03* |

*only added water is shown; composition also includes water accompanying IPA salt of glyphosate; total of all ingredients adds to 100%.

The following observations were made after storage for 24 hours at room temperature (Table 3.2).

TABLE 3.2

| Concentrate no. | Observation after 24 h at room temperature |
| --- | --- |
| 3-A | sedimentation |
| 3-B | no phase separation, no sedimentation |
| 3-C | no phase separation, sedimentation |
| 3-D | no phase separation, sedimentation |
| 3-E | no phase separation, sedimentation |
| 3-F | no phase separation, sedimentation |
| 3-G | top clearing, 25% of volume, sedimentation |
| 3-H | no phase separation, no sedimentation |
| 3-I | no phase separation, no sedimentation |

Although no longer-term stability studies were conducted, the initial results with concentrate 3-H, having a 44% by weight (approximately 480 g a.e./l) loading of glyphosate acid, exhibited good storage stability. By comparison, concentrate 3-G, having the same total glyphosate loading but with the glyphosate partly in the form of the IPA salt, was not stable. It is not clear why concentrate 3-F should have exhibited sedimentation after 24 hours, as a substantially identical composition in Example 1 (concentrate 1-K) exhibited no such sedimentation.

Example 4

Aqueous concentrate compositions of glyphosate were prepared by the procedures described for Example 3. All contained 10% by weight of Unithox™ 750. Glyphosate was present in the acid form, or in the form of the isopropylamine (IPA) salt, or as a mixture of both forms in various ratios, in a total amount of 31% acid equivalent by weight. In all compositions the balance to 100% by weight was water.

Composition of each of concentrates 4-A to 4-K is shown in Table 4.1.

TABLE 4.1

| Concentrate no. | Glyphosate a.e. total weight % | Glyphosate a.e. ratio IPA salt:acid | Unithox ™ 750 weight % |
| --- | --- | --- | --- |
| 4-A | 30.6 | 0:10 | 10.0 |
| 4-B | 30.6 | 1:9 | 10.0 |
| 4-C | 30.6 | 2:8 | 10.0 |
| 4-D | 30.6 | 3:7 | 10.0 |
| 4-E | 30.6 | 4:6 | 10.0 |
| 4-F | 30.6 | 5:5 | 10.0 |
| 4-G | 30.6 | 6:4 | 10.0 |
| 4-H | 30.6 | 7:3 | 10.0 |
| 4-I | 30.6 | 8:2 | 10.0 |
| 4-J | 30.6 | 9:1 | 10.0 |
| 4-K | 30.6 | 10:0 | 10.0 |

The following observations were made after storage for 24 hours at room temperature (Table 4.2).

TABLE 4.2

| Concentrate no. | Observation after 24 h at room temperature |
| --- | --- |
| 4-A | no phase separation, no sedimentation |
| 4-B | no phase separation, sedimentation |
| 4-C | no phase separation, sedimentation |
| 4-D | no phase separation, no sedimentation |
| 4-E | no phase separation, no sedimentation |
| 4-F | no phase separation, no sedimentation |
| 4-G | no phase separation, no sedimentation |
| 4-H | bottom clearing, 25% of volume, sedimentation |

TABLE 4.2-continued

| Concentrate no. | Observation after 24 h at room temperature |
| --- | --- |
| 4-I | bottom clearing, 50% of volume, amber color, sedimentation |
| 4-J | bottom clearing, 50% of volume, amber color, no sedimentation |
| 4-K | bottom clearing, 50% of volume, amber color, no sedimentation |

Concentrate 4-A, substantially identical to concentrates 3-F and 1-K, exhibited good initial stability. A corresponding concentrate made using glyphosate in the form of IPA salt rather than acid (concentrate 4-K) was not stable.

Concentrates 4-D to 4-G were placed in 5 ml glass vials and put in an oven at 50° C. Stability observations were made after 1 day (Table 4.3) and 5 days (Table 4.4).

TABLE 4.3

| Concentrate no. | Observation after storage for 1 day at 50° C. |
| --- | --- |
| 4-D | no phase separation |
| 4-E | no phase separation |
| 4-F | no phase separation |
| 4-G | starting to separate |

TABLE 4.4

| Concentrate no. | Observation after storage for 5 days at 50° C. |
| --- | --- |
| 4-D | no phase separation |
| 4-E | no phase separation |
| 4-F | starting to separate |
| 4-G | phase separation |

It was concluded that acceptably stable compositions were achieved only where glyphosate was present entirely or predominantly in the acid form.

Example 5

Aqueous suspension concentrate compositions of glyphosate acid were prepared by the procedure described for Example 2. All contained 31% by weight glyphosate acid and 10% by weight of an alkylether surfactant, either STA-30 or Unithox™ 480. Various additives were included at 1% by weight as shown in Table 5.1. In all compositions the balance to 100% by weight was water.

Particular care was taken in each case to continue blending the suspension concentrate until it had cooled to room temperature, because in a previous attempt where blending was terminated prematurely, the concentrates produced did not show their customary stability.

Composition of each of concentrates 5-B to 5-H is shown in Table 5.1. There was no concentrate 5-A.

TABLE 5.1

| Concentrate No. | Glyphosate acid weight % | Surfactant type | Surfactant weight % | Additive type | Additive weight % | Water weight % |
|---|---|---|---|---|---|---|
| 5-B | 30.65 | STA-30 | 10.00 | Aerosil 380 | 1.00 | 58.35 |
| 5-C | 30.65 | STA-30 | 10.00 | stearyl alcohol | 1.00 | 58.35 |
| 5-D | 30.65 | STA-30 | 10.00 | none | | 59.35 |
| 5-E | 30.65 | Unithox 480 | 10.00 | urea | 1.00 | 58.35 |
| 5-F | 30.65 | Unithox 480 | 10.00 | Aerosil 380 | 1.00 | 58.35 |
| 5-G | 30.65 | Unithox 480 | 10.00 | Unilin 425 | 1.00 | 58.35 |
| 5-H | 30.65 | Unithox 480 | 10.00 | none | | 59.35 |

The following observations were made after storage for 24 hours at room temperature (Table 5.2).

TABLE 5.2

| Concentrate no. | Observation after 24 h at room temperature |
|---|---|
| 5-B | phase separation, no sedimentation |
| 5-C | phase separation, sedimentation |
| 5-D | phase separation, sedimentation |
| 5-E | phase separation, no sedimentation |
| 5-F | no phase separation, no sedimentation |
| 5-G | no phase separation, no sedimentation |
| 5-H | no phase separation, no sedimentation |

It was concluded from the stability studies of Example 5 that physical stability of aqueous concentrate formulations of glyphosate acid with Unithox™ 480 was markedly superior to that of otherwise similar formulations using STA-30 in place of Unithox™ 480.

The preceding description of specific embodiments of the present invention is not intended to be a complete list of every possible embodiment of the invention. Persons skilled in the art will recognize that modifications can be made to the specific embodiments described here that would be within the scope of the present invention.

What is claimed is:

1. A concentrate composition for application to foliage of a plant to elicit a biological activity in said plant following dilution, dissolution or dispersion of said composition in water, said composition comprising
  (i) a plant treatment compound that is an acid having a solubility in deionized water at 25° C. of less than about 50 g/l, said plant treatment compound being present, predominantly in the acid form thereof, in an amount of about 20% to about 90% by weight, expressed as acid equivalent, of said composition; and
  (ii) a surfactant of formula

wherein R is a straight or branched chain aliphatic hydrocarbyl group having about 24 to about 60 carbon atoms and n is an integer having an average value of about 5 to about 100;
  the weight ratio of said surfactant to said plant treatment compound, expressed as acid equivalent, being about 1:2 to about 1:30.

2. A composition of claim 1 that further comprises water and is a liquid suspension concentrate composition having a continuous aqueous phase and a discontinuous particulate phase, wherein said plant treatment compound is present in an amount of about 240 to about 540 grams acid equivalent per liter of the composition, and wherein said discontinuous particulate phase is comprised predominantly of said plant treatment compound.

3. A composition of claim 2 wherein said plant treatment compound is a herbicide.

4. A composition of claim 3 wherein said herbicide is selected from acifluorfen, asulam, benazolin, bentazon, bialaphos, bispyribac, bromacil, bromoxynil, chloramben, clopyralid, 2,4-D, 2,4-DB, dalapon, dicamba, dichlorprop, diclofop, endothall, fenac, fenoxaprop, flamprop, fluazifop, fluoroglycofen, fluroxypyr, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, sulfamic acid, 2,3,6-TBA, TCA and triclopyr.

5. A composition of claim 3 wherein said herbicide is N-phosphonomethylglycine.

6. A composition of claim 5 wherein the amount of N-phosphonomethylglycine present is about 300 to about 540 grams acid equivalent per liter of the composition.

7. A composition of claim 5 wherein the amount of N-phosphonomethylglycine present is about 360 to about 480 grams acid equivalent per liter of the composition.

8. A composition of claim 5 wherein, in the formula for said surfactant, R is a linear saturated alkyl chain having 26 to 50 carbon atoms and n has an average value of about 10 to about 20.

9. A composition of claim 5 wherein the weight ratio of said surfactant to said N-phosphonomethylglycine, expressed as acid equivalent, is about 1:2 to about 1:6.

10. A composition of claim 5 wherein the weight ratio of said surfactant to said N-phosphonomethylglycine, expressed as acid equivalent, is about 1:3 to about 1:4.5.

11. A composition of claim 2 further comprising a long-chain hydrocarbyl alcohol in an amount of about 1% to about 5% by weight of the composition.

12. A composition of claim 8 further comprising a long-chain hydrocarbyl alcohol in an amount of about 1% to about 5% by weight of the composition, said long-chain hydrocarbyl alcohol having a linear saturated hydrocarbyl chain matching that of said surfactant.

13. A method of killing or controlling unwanted vegetation comprising diluting in a suitable volume of water a herbicidally effective amount of a composition of claim 3 to make a spray composition, and applying the spray composition by spraying to foliage of the unwanted vegetation.

* * * * *